United States Patent [19]

Jaggi et al.

[11] Patent Number: 4,845,552
[45] Date of Patent: Jul. 4, 1989

[54] QUANTITATIVE LIGHT MICROSCOPE USING A SOLID STATE DETECTOR IN THE PRIMARY IMAGE PLANE

[76] Inventors: Bruno Jaggi, 2180 Trafalgar Street, Vancouver, British Columbia, Canada, V6K 4M8; Mohammed J. Deen, School of Engineering Design, Simon Fraser Univ., Burnaby, B.C., Canada, V5A 1S6; Branko Palcic, 6012 Adera Street, Vancouver, British Columbia, Canada, V6M 3J4

[21] Appl. No.: 87,387

[22] Filed: Aug. 20, 1987

[51] Int. Cl.$^4$ ............................................. H04N 7/18
[52] U.S. Cl. ..................................... 358/93; 358/107; 382/6; 364/413.01
[58] Field of Search ................. 358/93, 211, 113, 227, 358/101, 107; 364/525, 413.08, 413.07, 413.01; 350/523, 300, 308; 382/6; 356/39

[56] References Cited

U.S. PATENT DOCUMENTS

| | | | |
|---|---|---|---|
| 1,316,050 | 9/1919 | Lidberg | 350/523 |
| 4,398,211 | 8/1983 | Young | 358/93 |
| 4,617,682 | 10/1986 | Mori et al. | 358/107 X |
| 4,633,504 | 12/1986 | Wihl | 358/106 X |
| 4,661,986 | 4/1987 | Adelson | 358/227 X |
| 4,672,559 | 6/1987 | Jansson et al. | 358/93 X |
| 4,680,635 | 7/1987 | Khurana | 358/101 X |
| 4,731,745 | 3/1988 | Katagiri et al. | 358/107 X |

Primary Examiner—James J. Groody
Assistant Examiner—Victor R. Kostak
Attorney, Agent, or Firm—Fetherstonhaugh & Co.

[57] ABSTRACT

A solid state microscope for viewing and scanning microscopic objects. The solid state microscope has a light source with a condensor and diffusion filter. A moveable stage is provided to allow X, Y, Z plane displacements in order to scan objects under the microscope. There is an objective to magnify the image of the object and project this image onto a two dimensional solid state image sensor. The solid state image sensor sends signals to an analog-to-digital converter where the signals are digitized and sent to a frame memory. A monitor is used to display the image of the object as stored in frame memory. The present invention can be interfaced with a computer to allow for automatic focusing and scanning of an image. The computer also houses storage means to store images. Methods of scanning an object are also described. A prism element can be used to obtain spectral scans of an object. In another scanning method, a first edge row of pixels is used to detect an object of interest in the scanned image. This first detection row activates an area of the sensor array at a later time to capture the entire image. In this way, only relevant information is collected and processed.

9 Claims, 7 Drawing Sheets

QUANTITATIVE LIGHT MICROSCOPE USING A SOLID STATE DETECTOR IN THE PRIMARY IMAGE PLANE

FIELD OF THE INVENTION

This invention relates to a solid state detector microscope and to a method of displaying and processing images. When the solid state detector is a charge-coupled device (CCD) the invention may be described as a CCD-microscope; in its general form the invention may be described as a solid state microscope.

DESCRIPTION OF THE PRIOR ART

For many applications where microscopy is used in biology, medicine, material science, etc., images have to be electronically captured and digitized for the purpose of storage or image processing. This task may be done using an optical microscope equipped with a video camera including those video cameras where a charge-coupled device (CCD) is used as the image sensor. The signals from the video camera are transformed into video signals, which can then be digitized using a frame grabber for further digital processing and then storage. Since video signals are analog signals they are not optimal for quantitative image processing. Furthermore, the optical paths in such systems are generally complicated: apart from the objective of the microscope, the light passes through beam-splitters or is reflected by semi-transparent mirrors and it then passes through at least one magnifying lens which can be an ocular or a projection lens. Hence, there are many optical elements through which the light must pass before it reaches the video detector. This introduces an inherent degree of distortion and aberration of the image.

Numerous digital image microscope devices of the above type are commercially available. A host of large and small companies provide a variety of options for image processing techniques. Examples include systems from Zeiss (IBAS 2000), Cambridge Instruments (Quantimet 920/970) and Leitz (TAS Plus). Indeed, such devices have found extensive use in material science and elsewhere. When used in cell biology and medicine, they are generally referred to as image cytometry devices. In most cases the image detector is a video camera from which a frame can be captured by a frame grabber. The digitized image can then be manipulated by a variety of techniques using computers or specialized imaging processors.

An alternate approach in capturing images is to use the dynamic microscope image processing scanner developed by Palcic, Jaggi and Nordin disclosed in U.S. Pat. No. 4,700,298. For this device, the image sensor is a solid state CCD device consisting of a linear array of photodetectors. The image can be acquired by moving the sample on a stage in one micron steps in a manner synchronized with capturing individual lines. Alternatively, the image can be scanned by moving the sensor across the magnified image. A similar approach to this method is found in U.S. Pat. No. 4,398,211 to Young which uses a linear solid state image sensor with a galvanometer scanning mirror (adding yet another mirror and a mechanical element to the system) for scanning in one of the two orthogonal directions while the sensor scans the other direction.

All the above systems suffer a significant degree of deterioration of the image due to the large number of optical elements in an optical microscope. Those systems which use video detectors suffer additional deterioration of the image because the transformation of the detected light intensities into a video signal represents a distortion of the original image. Also, many video cameras have an aspect ratio of typically 4:3. This makes computation of x, y functions of the image difficult (if it is at all performed) and generally further distorts the true image. Additional problems in quantitative microscopy using video cameras include interlacing and automatic gain control. The small field of view imposed by the microscope video systems makes it difficult to search visually for objects. In the case of acquiring images using scanning methods with a linear array, as with the dynamic microscope image processing scanner of U.S. Pat. No. 4,700,298 to Palcic et al. or U.S. Pat. No. 4,398,211 to Young, the image is digitized in discrete quantities and the pixels are squared. However, optical distortions due to the use of a microscope still exist, and most importantly, acquiring images in real time is generally not possible. A typical image can only be obtained in a few seconds.

Finally, even when one is able to obtain an image, irrespective of the time it takes or distortions it may have, one is in no position to know beforehand which part of the image is of interest and which part is not. For example, a small cell may exist in a large field of view; only the cell is of interest, yet most pixel data are of the background which holds no useful information. In a conventional system, the entire image has to be processed before one finds the object(s) of interest. This is a time consuming operation, generally preventing analysis of data in real time.

SUMMARY OF THE INVENTION

The present invention circumvents these problems by projecting the image directly, through one high resolution lens (an objective), onto a large two-dimensional CCD-aray or similar solid state image sensor. Accordingly, the present invention is a solid state microscope comprising:

a light source with a condensor and diffusion filter;

a moveable stage to provide X, Y and Z plane displacements to position and scan objects under the microscope;

an objective to magnify the image of an object and project it onto a two dimensional sold state image sensor;

a two dimensional solid state image sensor;

an analog-to-digital converter to provide real time digital images to the frame memory;

a frame memory;

a monitor to display the image of the object.

With the present invention, there is a minimum deterioration of the image as a single optical element (the objective) is used to project the image onto the solid state image sensor array located in the intermediate plane of the objective lens. The sensed discrete image is digitized, conditioned and processed in real time and displayed on a high resolution RGB-analog monitor. The solid state image sensor comprises a two dimensional array of individual detectors which are square pixels of a few micrometers. The discrete analog signals from individual pixels are directly digitized and are never transformed into a video signal. The signals from the entire array of detectors or from parts of the array can be processed and displayed on demand.

Selected individual lines or selected portions of the array can be captured, processed or stored. These local areas or pixels can be predetermined or they can be selected under dynamic conditions. In such applications, it may be advantageous if the two-dimensional detector array is a Charge Injection Device (CID). This solid state image sensor makes random access of pixels of the image particularly easy. For example, a processed signal of a pixel or a line of pixels could be used to trigger activation of a selected area of the array to capture an image limited to that area. In this way, only the minimum data needed for analysis of selected objects need be processed.

DESCRIPTION OF THE DRAWINGS

Aspects of the invention are illustrated, merely by way of example, in the accompanying drawings, in which.

DESCRIPTION OF THE PREFERRED EMBODIMENTS

Figure 1:
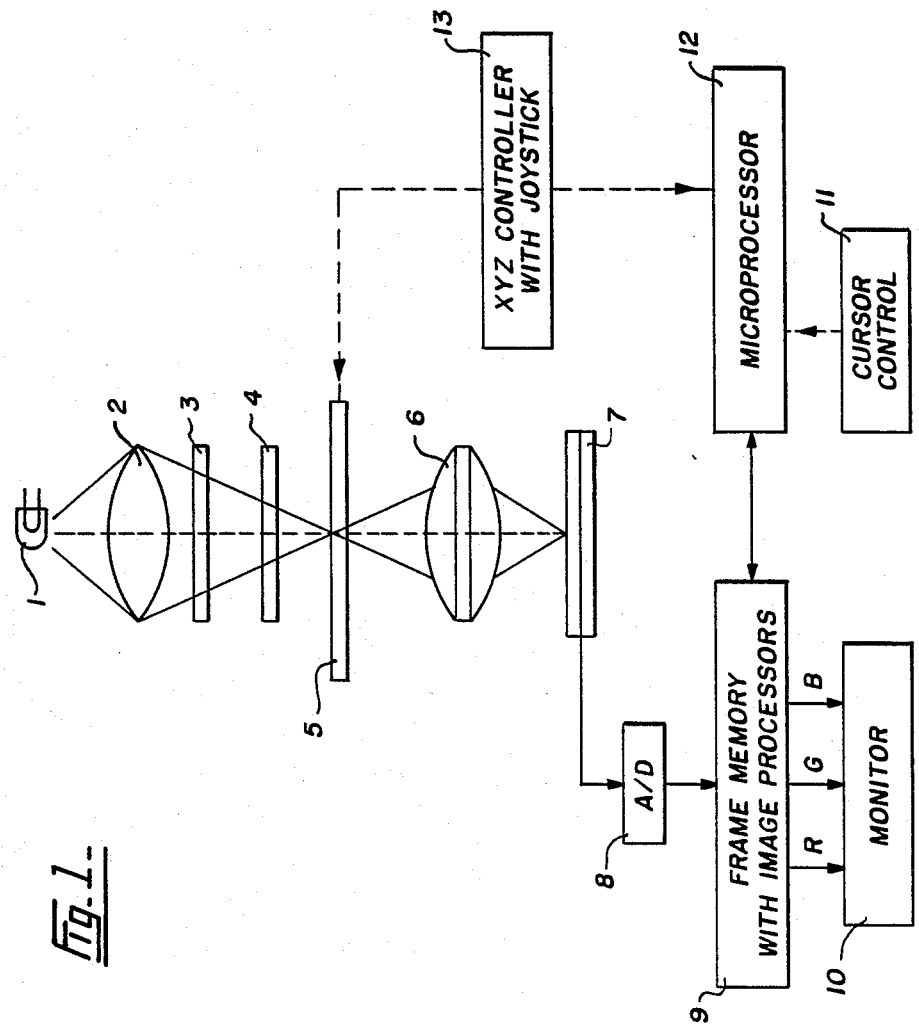
FIG. 1 is a schematic block diagram showing a preferred embodiment of the present invention which uses light transmitted through the object to be viewed to project an image onto the solid state sensor.
Figure 4:
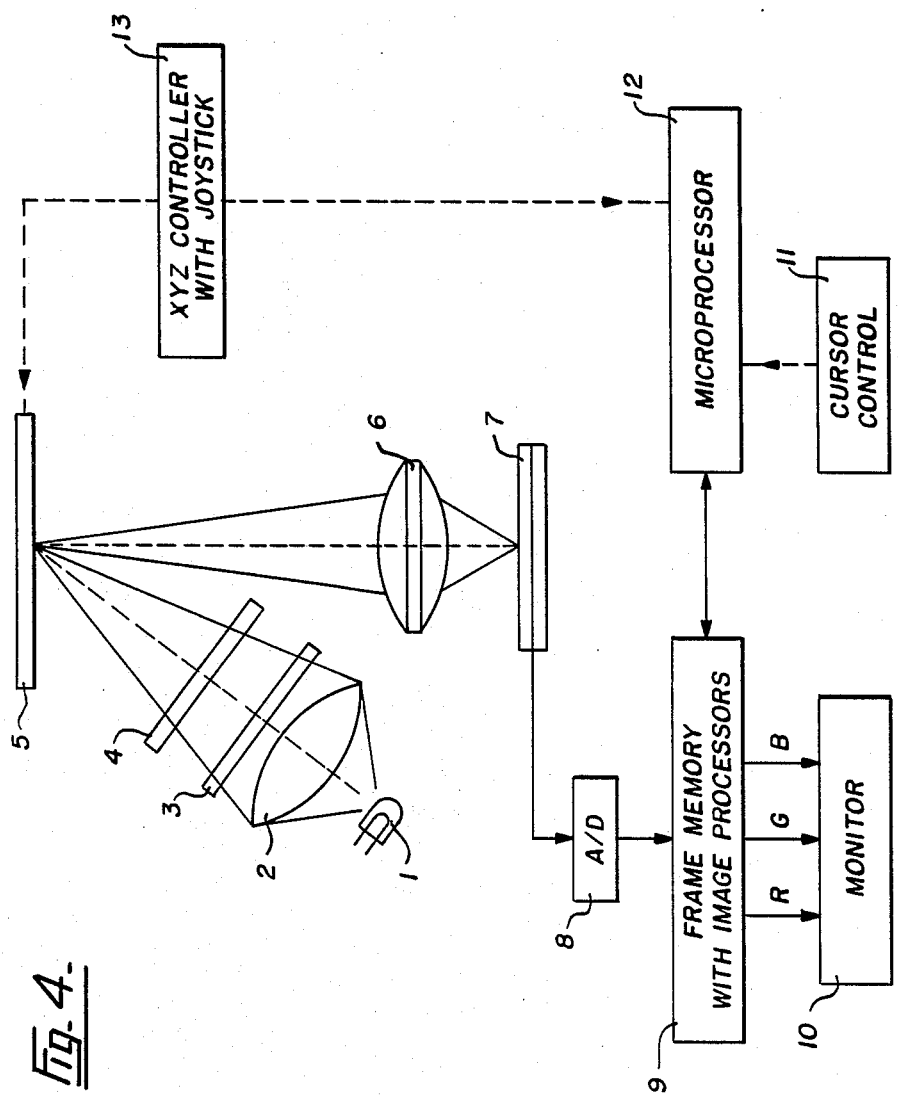
FIG. 4 is a schematic block diagram showing another embodiment of the present invention which uses light reflected from the object to be viewed to project an image onto the solid sensor.

Referring to FIG. 1, a transmittance mode embodiment of the present invention is shown schematically comprising a light source 1, with a condensor 2, diffusion filter 3 and optional filter 4, an x, y, z stage 6 which is driven by stepping motors, controlled by a controller 13 with a joystick, an objective 5, two-dimensional solid state image sensor 7, an analog-to-digital converter 8, a frame memory with image processors 20, a computer 12, a monitor 10, and a cursor control 11. FIG. 4 shows a reflecting light embodiment of the present invention in which the light source 1 illuminates the object to be viewed in such a way as to reflect the image of the object into the objective 5. The only difference between these two embodiments of the present invention is the arrangement of the light source 1, condenser 2, diffusion filter 3 and optional filter 4 relative to the object to be viewed.

The light source 1 is a powerful, stabilized light source, emitting from the near infrared to shorter wavelengths. Examples include a halogen or mercury source or a tunable laser. These light sources together with condensor 2 are commercially availble (e.g. Optikon Inc. or Nikon Canada Inc.) as are the stabilized power supplies e.g. Xantrex Technology Inc. or Kikusui Electronics Corp.). Whenever a light source of a selected spectrum is required, special filters 4, optical prisms or monochromators can be employed. For work in the ultra violet or infrared region of the electromagnetic spectrum, light sources of desired spectral output can be selected. Generally, the performance of the solid state image sensor 7 has to be matched to the selected wavelength of the selected light source 1.

It is desirable that stage 6 for holding a sample is motorized allowing precise step-wise movements in the x,y,z directions. In a preferred embodiment of the present invention, stage 6 is moved by stepping motors capable of movements of 0.1 micrometers, 0.25 micrometers or 1 micrometer per step, depending on the desired precision and velocity of the movements in x,y and z directions. Such motors are available from manufacturer's such as Gebruder Marzhauser, Wetzlar GmbH. Controller 13 controls the stepping motors, thereby controlling the number of steps, and the speed with which the steps are made including acceleration and decceleration of the stage 6. Present day controllers are capable of sending up to 20,000 steps per second in all three directions simultaneously (e.g. Lang-Electronik GmbH). Controller 13 is preferably under computer control to allow automatic focusing of the solid state microscope. Alternatively, stage 6 may be controlled using the joystick provided with controller 13 to allow manual movement of stage 6.

The objective 5 is a criticial part of the system. It is desirable that a changeable, large numerical aperture (N.A.) objective be used. Using visible light, the minimum distance between two adjacent points which can still be resolved is limited to approximately 0.15 micrometers. Optical resolution R is limited by the expression:

$$R = \frac{\lambda}{2 N.A.}$$

where $\lambda$ is the wavelength of the light source used. Hence, even a high power objective with a projection or ocular lens would not improve the theoretically achievable resolution of 0.15 micrometers, which can be provided by a low power, high numerical aperture objective using visible light. It is also important to use an objective 5 which gives a flat image in the intermediate image plane where the flat two-dimensional image sensor 7 is located. In the art of microscopy, the 'intermediate image plane' may also be referred to as to the primary image plane, the principal image plane, or the back focal plane of the objective. Objectives that deliver a flat image are known as Plan Apochromat lenses and are commercially available from companies such as Zeiss Canada Inc., Leitz-Wild AG, or Nikon Canada Inc. In the future, it should be possible to shape two dimensional arrays into curved surfaces, matching the focal surface of different objectives which do not focus intermediate images onto a flat plane.

For work in the ultraviolet (UV) region of the light spectrum, silica objectives 5 and condensors 2 must be employed to allow UV light to pass through the optics.

Together with the objective 5, the solid state image sensor 7 is the most important part of the solid state microscope. Only recent advances in CCD and VLSI (Very Large Scale Integration) technology have made lage arrays of sensors available. In a preferred embodiment of the present invention, the two-dimensional solid state image sensor is a Charge-Coupled Device (CCD) having over one million individual pixel elements in over 1,000 rows and over 1,000 columns of approximate size 10 micrometers×10 micrometers. Several such sensors are commercially available, e.g.: Texas Instrument 1024×1024 pixels with 10 micrometer×10 micrometer pixel elements; Kodak KAF1400, 1320×1035 pixels with 6.8 micrometer×6.8 micrometer pixel elements. Alternatively, a Charge-Coupled Photodiode (CCPD) or Charge Injection Device (CID) or any other two dimensional solid state image may be used provided the sensor yields sufficient spatial or photometric resolution. Preferably, the solid state image sensor 7 is cooled to provide a better signal-to-noise ratio, lower dark currents, decreased crosstalk and greater dynamic range, creating a more sensitive image sensor and making longer integration times possible. Cooling is achieved by thermo-electrical cooling devices (for example Marlow Industries, Inc). For much lower temperatures, e.g. below 240° K., a cryogenic cooling system can be employed (e.g. Cryosystems Inc.).

Figure 2:
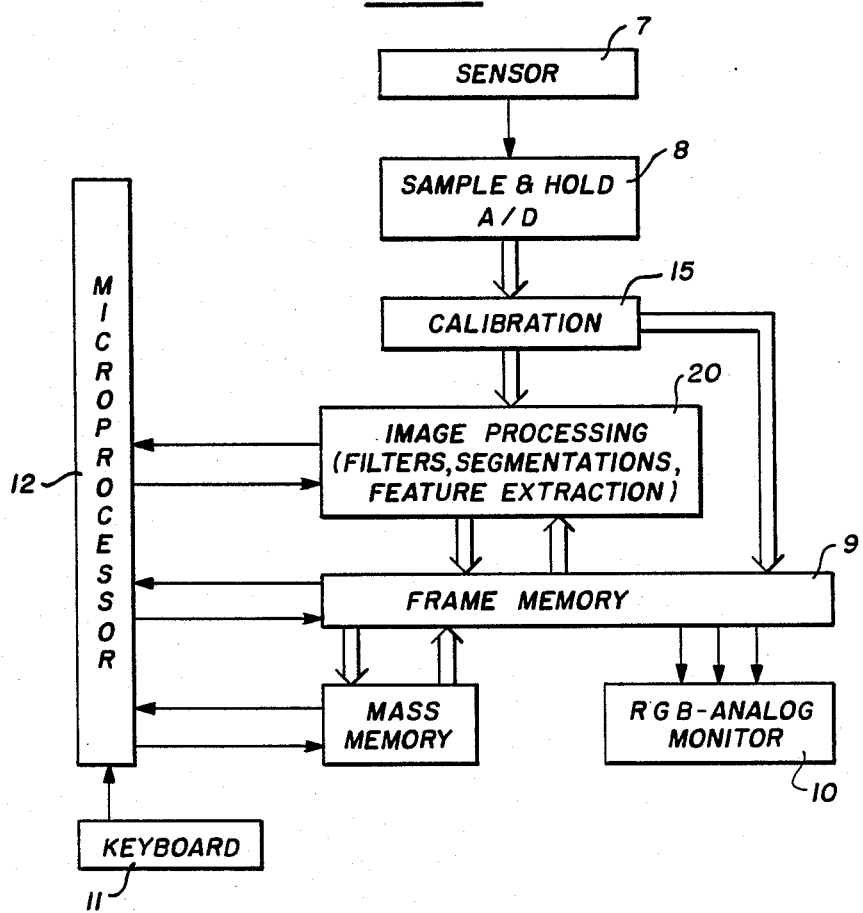
FIG. 2 is a simplified flow chart illustrating the operation of the solid state microscope.

When an image is projected onto the solid state image sensor 7, each pixel element of the sensor array generates a signal corresponding to the brightness level of the image light falling on the image sensor array. As shown in FIG. 2, the signals generated by the image sensor 7 are transferred to an analog-to-digital converter 8 where they are digitized in real time. The signals are then transferred to correction circuit 15 where they are corrected for electronic offset and gain. Such a correction circuit allows one to fully calibrate the system taking into account optical and detection induced distortions. In a preferred embodiment, each image is calibrated in real time. This is achieved by subtracting and normalizing the background image and correcting the signal using the formula:

$$I_c = K \frac{I_i - I_d}{I_b - I_d}$$

Where $I_c$ is the calibrated (sometimes described also as de-calibrated) image, $I_i$ is the uncorrected image, $I_b$ is the image of the background light without an object (bright image) and $I_d$ is the image of complete darkness (dark image) of each pixel; K is a constant. In this way, uneven illumination, imperfection of the objective and uncorrected signal amplification of the solid state imaging array are eliminated from the calibrated image. After treatment by the correction circuit 15, the calibrated digital image is continuously downloaded into a frame memory unless the image is held for measurement.

The frame memory 9 with associated image processor(s) 20 must be capable of processing and displaying data in real time. The image processors 20 provide filtering and feature extraction processing (e.g. filtering, convolutions, FFTs, etc.) in order to produce an image suitable for display on RGB analog monitor 10. Also, signal averaging should be available for better quality of images. Such image processors for video systems are already commercially available (e.g. MVP-AT/NP, Matrox Electronic Systems Inc.) and similar processors can be built with a direct pixel by pixel digitization.

Colour information about the object, for viewing as well as for image processing purposes, can be achieved in several ways. In a preferred embodiment, three images are obtained in sequence using red, green and blue bandwidths as the light source. The three images are then combined into an RGB-analog signal. Other alternatives include the use of several detectors or using only a portion of a single detector for each colour. Colour and/or spectral information can be used to selectively detect or outline objects of the image and to characterize the image.

The images produced by the image processors 20 are displayed on a high resolution RGB-analog monitor 10 where the whole image or a part of the image can be viewed; hence no ocular lens is required. This type of viewing is more convenient and in addition the actual digital image on which the measurements are performed is observed rather than the optical image. The monitor image can be overlayed with a cursor to allow for measuring and selecting objects of interest. Such a cursor would be manipulated using cursor control 11 operating through computer 12. Ideally, the bandwidth of the monitor 10 is approximately matched to the number of pixels on the image sensor array 7. The pixel rows are displayed in a non-interlaced fashion and at a data rate of 1/60 to reduce flicker. In this way, one can view individual pixels of the array directly without any distortion.

The computer 12 serves to control various aspects of the present invention and acts as an operator input-output device. Very little, if any, data manipulation is performed by the computer, and thus, in a preferred embodiment the computer can be any 80386 based personal computer. The computer also serves as a storage device for images or parts of images if required. A variety of mass storage devices are commercially available, the most appropriate being optical memory disk recorders or WORM (Write Once Read Many) recorders due to their large memory capacity and nondestructive way of retrieving information.

Focusing of the solid state microscope can be achieved automatically under computer control by using the frequency information of the detected signal. Focus can be defined as the highest frequency content of the image as measured by a variety of computer calculated algorithms including a Fourier Transformation of the solid state sensor signals. Stage controller 13 under computer control can move stage 6 in the Z direction in order to achieve autofocus. As well, focusing can be done manually by overriding computer control using the joystick of stage controller 13.

Autofocus is also possible while scanning an object on stage 6. During scanning, the stage is moved in the X and Y directions causing the image projected onto the solid state sensor 6 to change. In this case, the first rows at the edge of the stage image sensor array 7 are used to process data of the newly scanned image, before the object is "seen" by the rest of the pixel elements of the two dimensional detector. The processed signals of the first few pixel rows are then used to correct the focus through computer control of the stage 6. While scanning, the edge rows of the sensor array are continuously obtaining data for the focusing routine of the computer to analyse and make appropriate adjustments. This is particularly useful when large surfaces are scanned which do not lie in an optically flat surface parallel to the plane of scanning.

Alternatively, in a different embodiment of the present invention, the objective 5 can be moved in the Z direction either manually or under computer control for focusing purpose.

In use, the various embodiments of the present invention have several applications.

In its most simple and straight forward use, the present invention can be used as a conventional microscope according to the embodiments shown in FIGS. 1 and 4 where the image of the object being viewed is projected through the objective 5 and focused on the solid stage image sensor 7. The signals generated by the image sensor are immediately digitized and displayed with a frequency of no less than 60 Hertz on an RGB analog monitor. FIG. 1 shows an embodiment of the present invention that transmits light through the object being viewed. In such a transmittance mode, the present invention can be used for measuring relative absorbance and transmittance of objects. The embodiment of FIG. 4 uses light reflected from the object being viewed to create an image on the image detector array. All modes of reflective microscopy are possible, similar to those in ordinary microscopy. The solid state microscope can be readily adopted to measure integrated fluorescence or the distribution of fluorescence over an object.

Using appropriate objectives and/or illumination modes of a specimen, phase contrast, Nomarski, dark field and other microscopy techniques can be performed. It is possible to measure absorbance of a specimen by examining the object using both the light transmitting and reflecting embodiments of the present invention to obtain transmissions and reflective spectra. From these spectra, corrected absorbance can be calculated.

Figure 3:
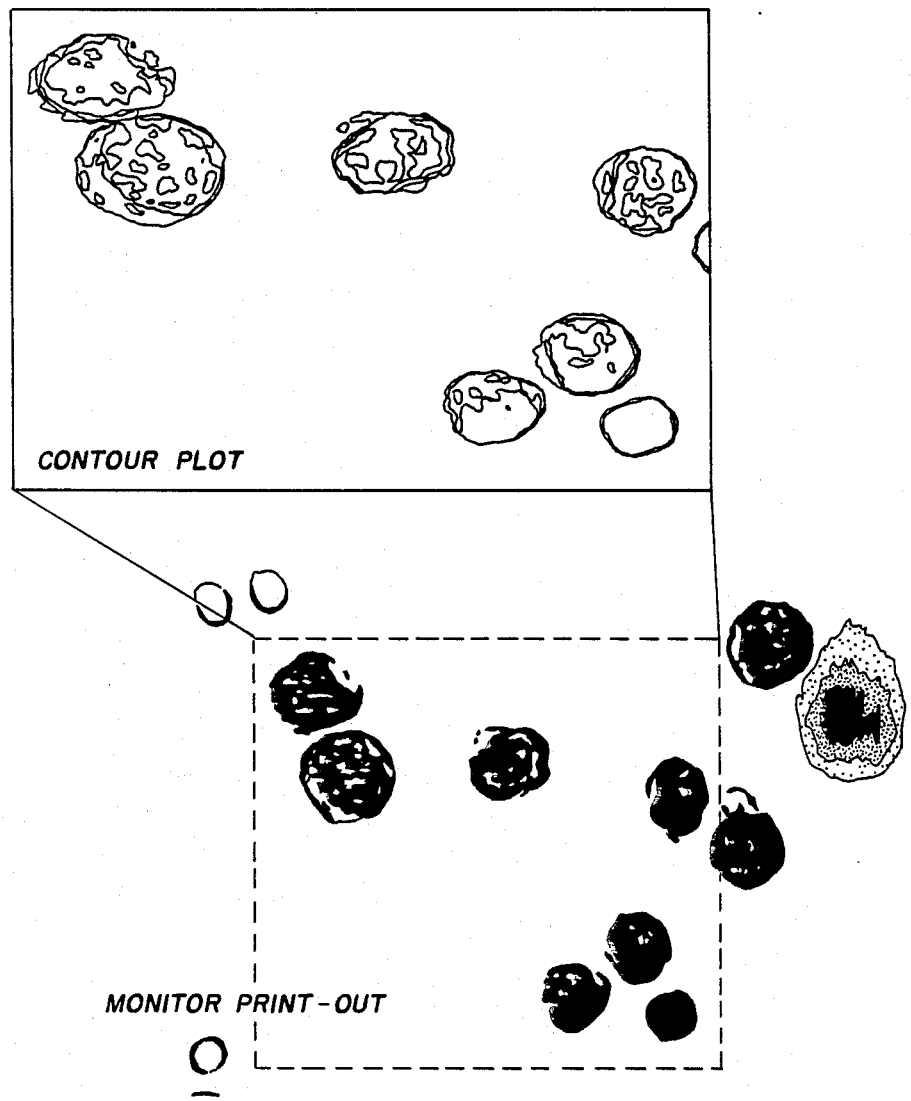
FIG. 3 shows a monitor printout of stained human red and white blood cells as viewed using the present invention with a 3 level contour plot of a portion of the monitor printout also shown.

No matter which embodiment of the solid state microscope is used, the image acquired by the solid state image sensor 7 is processed in real time. FIG. 3 shows a monitor image of stained human red and white blood cells obtained using the present invention. The image 35 was calibrated by circuit 15 as described previously and filtered by image processors 20 using a medium filter to reduce high frequency noise. Employing appropriate segmentation techniques available through the image processors 20, the objects of interest can be outlined as contour plots as shown in FIG. 3 where the portion of the monitor screen outlined by dashed lines has been processed in such a manner.

Figure 5:
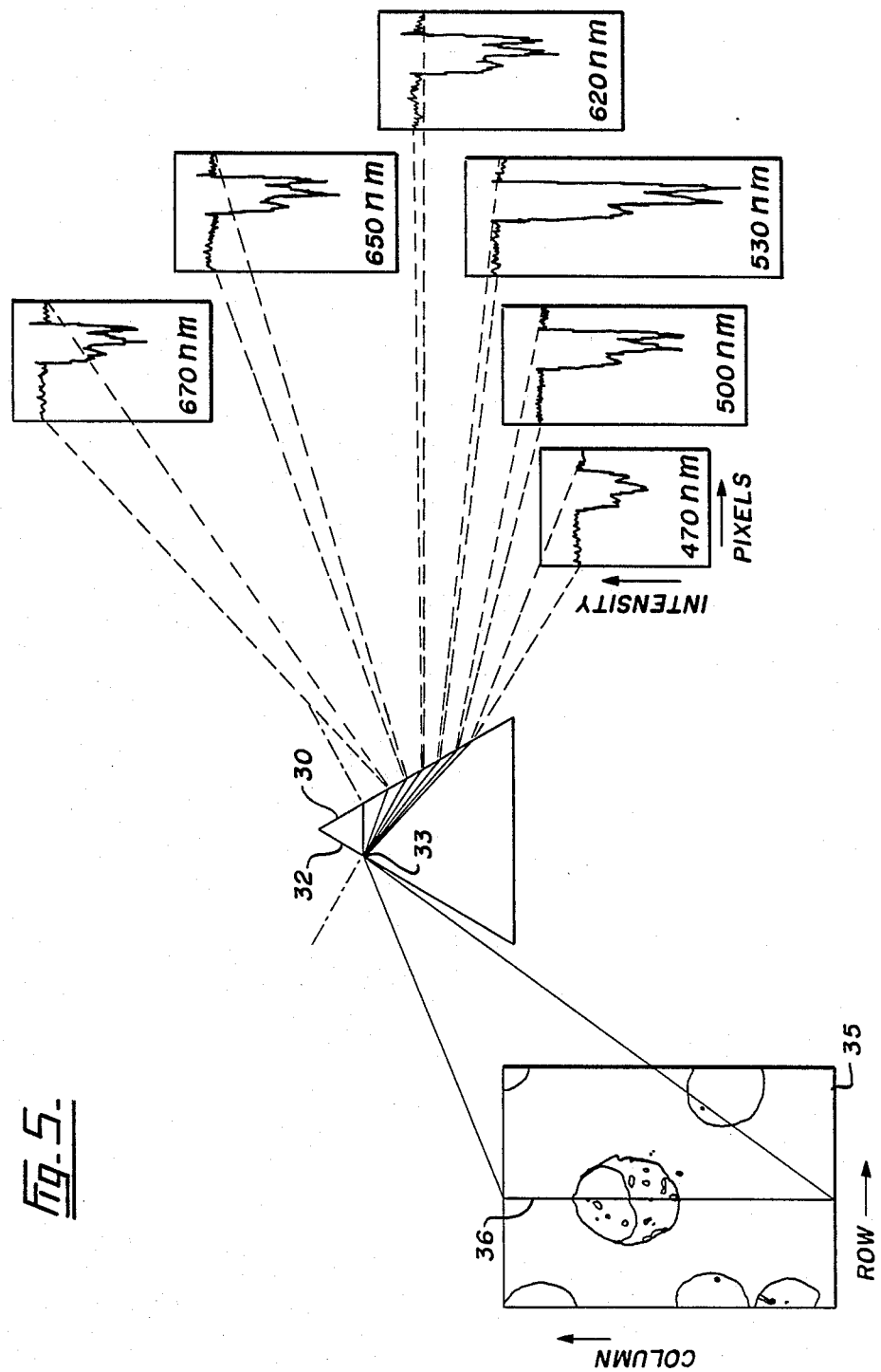
FIG. 5 shows a further embodiment of the present invention which utilizes a prism to project spectral scanlines of an object onto the solid state sensor.
Figure 6:
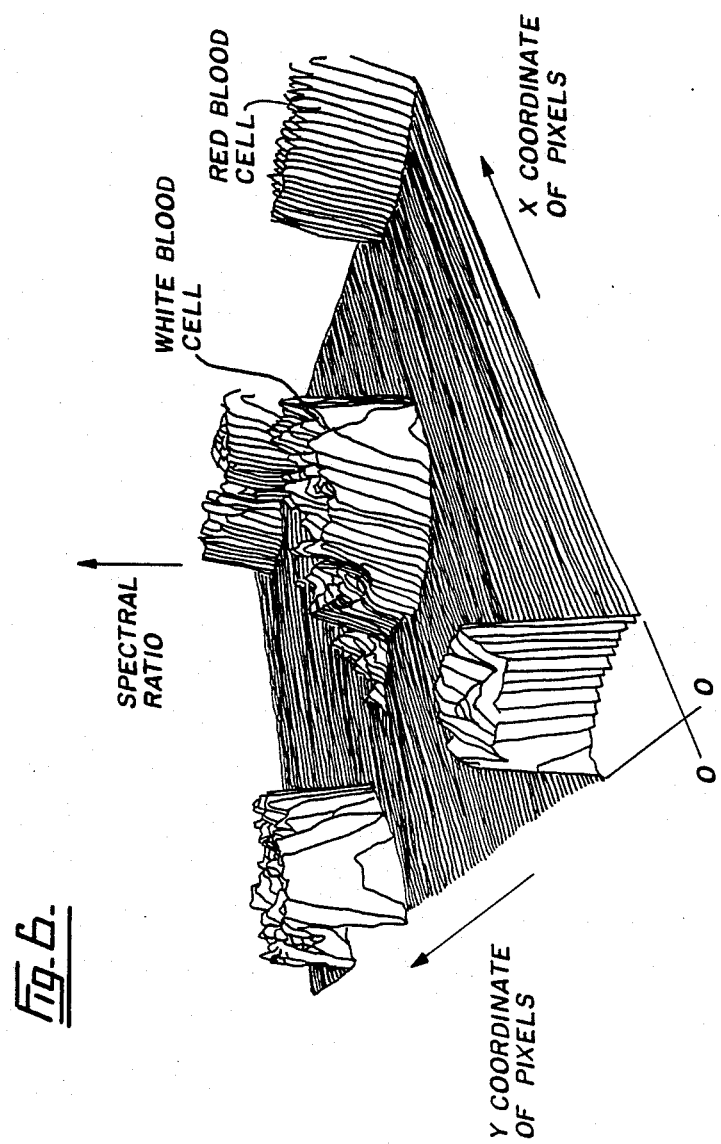
FIG. 6 is a two dimensional image of white and red blood cells generated using spectral scanlines of two different wavelenths as shown in FIG. 5.

In another embodiment, the present invention can be used to generate spectral scanlines of various wavelengths of a specimen. This particular embodiment of the invention is a modification of the solid state microscope of FIG. 4 and includes a prism element mounted between the objective 5 and the solid state sensor array 7. FIG. 5 is a schematic diagram illustrating the process involved. The prism element 30 is covered by a light absorbing material on surface 32 except in a very narrow band 33 a few microns wide, corresponding to the width of one row of pixel elements on the CCD array 7. Surface 32 of prism 30 faces objective 5 and the image 35 of a specimen is projected onto surface 32. Only that portion of image 35 that corresponds with narrow band 33 will be transmitted through the prism. Therefore, narrow band 33 transmits a single scanline 36 across image 35 through prism 30 to image sensor array 7. As scanline 36 passes through 30 it is broken into a spectrum of various wavelengths. Image sensor array 7 is positioned behind prism 30 such that each spectrum wavelength is projected onto a row of pixels. This spectral information is detected a digitized and further processed to produce the spectral diagrams of various wavelengths shown on the right of FIG. 5 which are plots of the light intensity at a particular wavelength across a particular scanline 36 of image 35. If necessary this spectral information can be stored. In FIG. 5 a white blood myeloblast cell is being processed according to the above procedure. If desired, an image of interest can be scanned by moving the stage 6 using appropriate step sizes to produce a complete set of scanlines 36 across an image 35. For example, a fixed stain cell on a microscope slide can be scanned by moving the stage 6 in the X direction while the Y direction is projected as a scanline 36 onto the solid state sensor 7 and stored in memory. FIG. 6 shows a composed image created using some of the spectral information generated by the above scanning procedure. FIG. 6 shows a composed image as a normalized ratio of two sets of spectral lines of approximately 470 nm and 530 nm taken across image 35 of FIG. 5. It is possible to image any other mathematical function of two or more sets of spectral lines of the selected object.

When using the solid state microscope of the present invention individual pixels, sets of pixels (e.g. are part or the whole of a row or column) or a selected area of the single sensor array (e.g. a square or a rectangle of pixels) can be specified in an addressable form such that only signals from the addressed pixels are processed and displayed. In such an application, it is desirable that the two dimensional sensing array is a Charge Injection Device (CD) which makes random access to local areas of the image particularly easy. This selection of certain pixels can be achieved under dynamic conditions.

For example, during scanning of a specimen, as the stage 6 is moved causing the image projected on the solid state image sensor 7 to move across the sensor, a first edge row of pixels is used to detect objects of interest and subsequently activate a selected area of the two dimensional array where a complete image of the object of interest will fall at a later time dependent on the scanning speed of the solid state microscope. In this way, an edge row of pixels across the solid state sensor array is used as an image detector while the pixel array behind the front row is used to capture the image to be processed. This is particularly useful when a large area is scanned containing few objects of interest. The front edge row signals of the solid state sensor array are used for coarse feature extraction of the object, while the activated area within the array is used for fine feature extraction. Thus, both coarse and fine features of cells can be extracted in one and the same scan.

Figure 7:
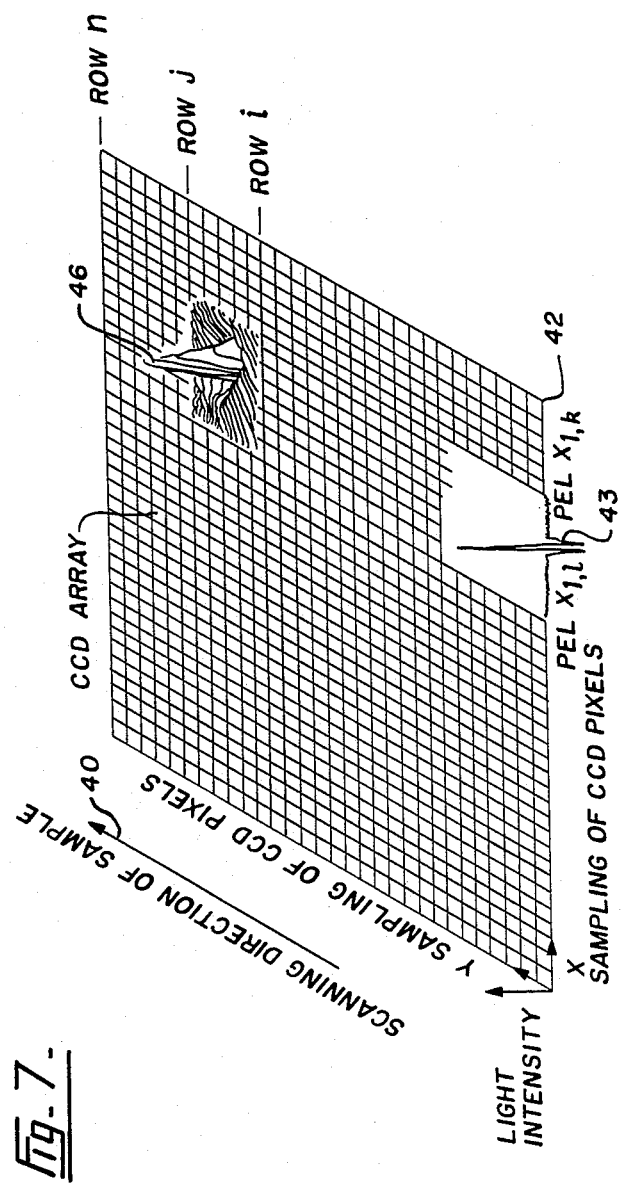
FIG. 7 illustrates the solid state sensor scanning method of the present invention where only that part of the array containing the image of the object of interest is processed by the solid state microscope.

This technique of single line detection followed by image acquisition is particularly useful for scanning for unstained live cells growing far apart in a tissue culture vessel. FIG. 7 showing a solid state sensor array divided into rows (i,j) and columns (k,l) demonstrates this procedure. As a sample is moved on stage 6 in the direction of arrow 40, the front row 42 of pixels is used to detect signals which are analyzed in real time. If a signal is detected indicating an object of interest which warrants examination in further detail, an area of pixels is activated at a later time which captures the image of interest and processes the image extensively including storage of the image in memory. Representative signals generated by objects of interest will have been previously collected and appropriate software routines will compare incoming signals with representative signals to determine when a match occurs. The object of interest is "seen" by another portion of the two dimensional sensor array after a time delay. Depending on the scanning speed and the size of the object of interest, which can be estimated from the incoming data of the first row 42 of pixels, the number of pixels and the location of pixels to be activated can be determined such that only data belonging to the object of interest is collected and processed. In this way, only relevant information is processed saving time and memory space. In FIG. 7, a signal 43 is being detected between pixel elements $X_{1,k}$ and $X_{1,l}$ (where the subscripts represent rows and columns in the sensor array) causing area 46 of the sensor array to be activated at a later time to capture the image of the object.

The present invention provides a number of important technical advantages which can be summarized as follows:

1. Simple optical path;
2. High resolution;
3. Large field of view;
4. Microscope image display on the monitor overlayed with graphics for cursor measurements;
5. Direct access to any part of the digital image;
6. Flexibility in scanning modes;
7. Various means to acquire spectral information and/or low light level images;
8. Operation in light reflecting absorption modes for surface investigations;
9. Movements of light transmission, absorbance, reflection, scatter and fluorescence.
10. Low cost.

We claim:

1. A solid state microscope comprising:
   a light source with a condensor and diffusion filter;
   a movable stage to provide X, Y and Z displacements to position and scan an object under the microscope;
   an objective being highly corrected for abberations with a large numerical aperture and an ultrawide flat field to produce and project magnified images of the object onto a two dimensional solid state image sensor positioned in the primary image plane of the objective, the image sensor having a large sensing area with a high pixel density and generating signals corresponding to the spatial distribution of the brightness levels of the images;
   an analog-to-digital converter associated with the solid state image sensor to process and convert the signals of the solid state image sensor to provide real-time digital images of the object;
   calibration and correction means coupled to said analog-to-digital converter for enhancement of the real-time digital images to account for optical and detection induced distortions;
   a frame memory coupled to said calibration and correction means into which the real-time digital images are continuously downloaded;
   image processors associated with the frame memory for processing the real-time digital images into a display image; and
   display means coupled to the image processors for displaying the display image generated by the image processors.

2. A solid state microscope as claimed in claim 1 including a computer serving as the system controller and as an operator input-output device, said computer having a mass storage device for storing the digital images of the frame memory.

3. A solid state microscope as claimed in claim 1 in which said light source, condensor, and diffusion filter are positioned so as to transmit light through the object being viewed.

4. A solid state microscope as claimed in claim 1 in which said light source, condensor, and diffusion filter are positioned so as to reflect light from the object being viewed.

5. A solid state microscope as claimed in claim 1 in which said solid state image sensor is a two dimensional charge-coupled device (CCD) larger than $1000 \times 1000$ pixels having a pixel density of 10,000 pixels per square millimeter.

6. A solid state microscope as claimed in claim 1 in which said display means is a high resolution monitor.

7. A solid state microscope as claimed in claim 1 in which a prism element is positioned in front of the solid state image sensor, said prism element allowing only a single horizontal scanline to be projected onto the image sensor, this single scanline being broken in the vertical direction into spectral lines by the prism so that each point of the scanline is projected onto a different row of the solid state image sensor, the spectral line information being digitized and stored in the frame memory.

8. A method of scanning an object using a solid state microscope comprising:
   a light source with a condensor and a diffusion filter;
   a moveable stage to provide X, Y and Z displacements to position and scan an object under the microscope;
   an objective being highly corrected for abberations with a large numerical aperture and an ultrawide flat field to produce and project magnified images of the object onto a two-dimensional solid state image sensor positioned in the primary image plane of the objective, the image sensor having a large sensing area with a high pixel density and generating signals corresponding to the spatial distribution of the brightness levels of the images;
   an analog-to-digital converter associated with the solid state image sensor to process and convert the signals of the solid state image sensor to provide real-time digital images of the object;
   calibration and correction means coupled to said analog-to-digital converter for enhancement of the real-time digital images to account for optical and detection induced distortions;
   a frame memory coupled to said calibration and correction means into which the real-time digital images are continuously downloaded;
   image processors associated with the frame memory for processing the real-time digital images into a display image; and
   display means coupled to the image processors for displaying the display image generated by the image processors;
   a prism element between the solid state image sensor and the moveable stage;
   the method being used to obtain spectral information about an object and the method comprising:
   projecting an image of the object onto the prism, the prism allowing only a single scanline to be transmitted to the image sensor, this single scanline being broken into spectral lines of different wavelengths by the prism;
   positioning the image sensor such that different spectral lines are projected onto different rows of detectors of the solid state image sensor;
   digitizing and storing the different spectral lines in frame memory;

moving the stage to scan the next line of the object; and repeating the above steps until the entire object has been scanned to create sets of spectral lines of different wavelengths.

9. A method as claimed in claim 8 involving combining two or more sets of spectral lines of an object using a mathematical function to create a spectral image of the object.

* * * * *